United States Patent
Nielsen et al.

(10) Patent No.: US 8,677,762 B2
(45) Date of Patent: Mar. 25, 2014

(54) COMBINED PRODUCTION OF HYDROCARBONS AND ELECTRICAL POWER

(75) Inventors: Poul Erik Højlund Nielsen, Fredensborg (DK); Thomas Rostrup-Nielsen, Holte (DK); Bodil Voss, Virum (DK); Finn Joensen, Hørsholm (DK)

(73) Assignee: Haldor Topsoe A/S, Lyngby (DK)

( * ) Notice: Subject to any disclaimer, the term of this patent is extended or adjusted under 35 U.S.C. 154(b) by 1071 days.

(21) Appl. No.: 12/674,272

(22) PCT Filed: Aug. 13, 2008

(86) PCT No.: PCT/EP2008/006648
§ 371 (c)(1),
(2), (4) Date: Feb. 19, 2010

(87) PCT Pub. No.: WO2009/033542
PCT Pub. Date: Mar. 19, 2009

(65) Prior Publication Data
US 2011/0314834 A1    Dec. 29, 2011

(30) Foreign Application Priority Data
Sep. 14, 2007 (DK) ................................. 2007 01326

(51) Int. Cl.
*F02C 6/18* (2006.01)
(52) U.S. Cl.
USPC .............................................. 60/780; 60/772
(58) Field of Classification Search
USPC ................... 60/780, 772, 39.01, 777, 723
See application file for complete search history.

(56) References Cited

U.S. PATENT DOCUMENTS

| | | | |
|---|---|---|---|
| 4,011,275 A | 3/1977 | Zahner | |
| 4,481,305 A | 11/1984 | Jorn et al. | |
| 5,133,180 A * | 7/1992 | Horner et al. | 60/39.12 |
| 5,165,224 A * | 11/1992 | Spadaccini et al. | 60/780 |
| 5,177,114 A | 1/1993 | Van Dijk et al. | |
| 5,937,631 A * | 8/1999 | Holm-Larsen et al. | 60/780 |

FOREIGN PATENT DOCUMENTS

| | | |
|---|---|---|
| EP | 0 020 140 A1 | 12/1980 |
| WO | WO 97/30011 A1 | 8/1997 |
| WO | WO 03/035591 A1 | 5/2003 |
| WO | WO 03/062142 A1 | 7/2003 |

* cited by examiner

*Primary Examiner* — Phutthiwat Wongwian
*Assistant Examiner* — Vikansha Dwivedi
(74) *Attorney, Agent, or Firm* — Dickstein Shapiro LLP

(57) ABSTRACT

A process for the preparation of hydrocarbon products and for the generation of power that includes the steps of (a) providing a synthesis gas having a hydrogen to carbon monoxide ratio of between 0.1 and 1; (b) contacting the synthesis gas with one or more catalysts which together catalyse a reaction of hydrogen and carbon monoxide to oxygenates comprising methanol and dimethyl ether with a dimethyl ether to methanol ratio of higher than 2 and a carbon dioxide content of above 20 mole %; (c) contacting the carbon dioxide containing oxygenate mixture at an inlet temperature of between 240° and 4000° C. with a catalyst being active in the conversion of oxygenate to higher hydrocarbons and a tail gas being rich in carbon dioxide; (d) combusting the carbon dioxide rich tail gas in a gas turbine combustion chamber to flue gas; and (e) expanding the flue gas stream through a gas turbine for the generation of power.

7 Claims, 2 Drawing Sheets

COMBINED PRODUCTION OF HYDROCARBONS AND ELECTRICAL POWER

FIELD OF THE INVENTION

This invention relates to a process for the combined production of hydrocarbons, especially gasoline, and power.

In particular, the invention concerns an improved combination of process steps for the production of gasoline by gasification of solid carbonaceous material, which gasoline production is integrated into a combined cycle power plant.

BACKGROUND OF THE INVENTION

Carbon monoxide rich synthesis gases with hydrogen to carbon monoxide ratios below or around 1.5, typically below 1, are produced by gasification of coal, petroleum coke, oils and biomass. For the purpose of conversion of the carbon monoxide rich synthesis gas into chemicals and/or fuels a pre-adjustment of the synthesis gas with respect to hydrogen to carbon monoxide ratio and carbon dioxide content is typically performed in order to meet the required stoichiometry for the desired product. Pre-adjustment may involve one or more of the steps of water gas shift, adjustments by membranes or washes and purging. As very often the desired hydrogen to carbon monoxide ratio of the synthesis gas utilised is well above 1 a typical means of synthesis gas adjustment is the water gas shift conversion followed by removal of excess $CO_2$ e.g. by absorption in a liquid medium by well known processes such as the Rectisol®, Selexol® or methyl diethanol amine (MDEA) washes. A disadvantage of these processes is that large amounts of carbon dioxide are vented.

The synthetic gasoline process as an example is known to take place in two steps: the conversion of synthesis gas to oxygenates and the conversion of oxygenates to gasoline product. These process steps may either be integrated, producing an oxygenate intermediate, e.g., methanol or methanol dimethyl ether mixtures, which along with unconverted synthesis gas is passed in its entirety to the subsequent step for conversion into gasoline (J. Topp-Jørgensen, Stud. Surf. Sci. Catal. 36 (1988) 293) or the process may be conducted in two separate steps with intermediate separation of oxygenates, e.g. methanol or raw methanol (S. Yurchak, Stud. Surf. Sci. Catal. 36 (1988) 251).

Preferred oxygenates include methanol, dimethyl ether and higher alcohols and ethers thereof, but also oxygenates like ketones, aldehydes and other easily convertible oxygenates may be applied.

In either case conversion of synthesis gas to oxygenates involves heat development in that both the conversion of synthesis gas to oxygenate and the further conversion of oxygenate to gasoline product are exothermic processes.

An integrated Fischer-Tropsch (FT) process and power production from carbonaceous materials by passing the material through a syngas generation unit, an air separation unit, a Fischer-Tropsch unit, a $CO_2$ removal unit and a combined cycle electricity generation unit is disclosed in U.S. Pat. No. 6,976,362. Produced carbon dioxide is collected for sale or sequestration up stream of the electricity generation unit.

The production of gasoline by the integrated process scheme is also discussed in U.S. Pat. No. 4,481,305. Hydrocarbons and especially as gasoline are prepared by catalytic conversion in two subsequent reactors of a synthesis gas containing hydrogen and carbon oxides and having a mole ratio $CO/H_2$ above 1 and when the conversion commences a mole ratio $CO/CO_2$ of 5 to 20. Synthesis gas is converted with high efficiency in a first step into an oxygenate intermediate comprising predominantly dimethyl ether (DME) said mixture being converted in a second step into gasoline by the net reaction scheme

$$3H_2+3CO \rightarrow CH_3OCH_3+CO_2+\text{Heat} \quad (1)$$

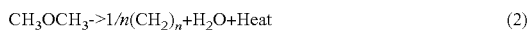
$$CH_3OCH_3 \rightarrow 1/n(CH_2)_n+H_2O+\text{Heat} \quad (2)$$

$(CH_2)_n$ represents the wide range of hydrocarbons produced in the gasoline synthesis step. After separation of the hydrocarbon product, unconverted synthesis gas comprising hydrogen and carbon oxides is recycled to the oxygenate synthesis step after $CO_2$ is at least partly removed in a $CO_2$ wash.

SUMMARY OF THE INVENTION

The general object of the invention is to provide an improved integrated process scheme for the preparation of valuable hydrocarbons, such as gasoline and light petroleum gas (LPG) from carbon monoxide rich synthesis gas having a composition typical for gases produced by gasification of solid carbonaceous material without the requirement that the synthesis gas be pre-adjusted with respect to hydrogen to carbon monoxide ratio and without the requirement that $CO_2$ be removed from the synthesis gas feed stream prior to entering into the hydrocarbon synthesis step.

Consequently, the invention provides in its broadest embodiment a process for the preparation of hydrocarbon products and for the generation of power, comprising the steps of
(a) providing a synthesis gas having hydrogen to carbon monoxide ratio of between 0.1 and 1;
(b) contacting the synthesis gas with one or more catalysts which together catalyse a reaction of hydrogen and carbon monoxide to oxygenates comprising methanol and dimethyl ether with a dimethyl ether to methanol ratio of higher than 2 and a carbon dioxide content of above 20 mole %;
(c) contacting the carbon dioxide containing oxygenate mixture at an inlet temperature of between 240° C. and 400° C. with a catalyst being active in the conversion of oxygenate to higher hydrocarbons and a tail gas being rich in carbon dioxide;
(d) combusting the carbon dioxide rich tail gas, optionally admixed with fresh carbon monoxide rich synthesis gas in a gas turbine combustion chamber to flue gas; and
(e) expanding the flue gas stream through a gas turbine for the generation of power.

The combined MeOH/DME synthesis provides relatively high conversion per pass and enables integration of the syngas-to-gasoline process into a single loop as opposed to the known MTG process which requires two separate synthesis loops: Syngas to MeOH and MeOH to gasoline.

The favourable thermodynamics at low $H_2$: CO ratios enable the methanol/DME synthesis to be carried out at much lower pressure compared to methanol synthesis. When highly active catalysts are applied efficient conversion is reached at 30-40 bars.

At CO-rich conditions the water gas shift reaction induces a strong enhancement of conversion due to favourable thermodynamics because water formed in the oxygenate production step is shifted virtually completely by reaction with CO to form hydrogen and carbon dioxide. The net reaction then becomes essentially that of hydrogen+carbon monoxide to DME+CO2.

Another aspect relating to the favourable thermodynamics in the combined methanol and DME synthesis is that a 'oncethough' layout is applicable, which is particularly advantageous in the co-generation of gasoline in IGCC plants. Single-pass conversions of more than 50% of the $H_2+CO$ may be achieved, while unconverted synthesis gas is applied for power generation.

The synthesis of hydrocarbons and/or fuels such as dimethyl ether, higher alcohols and gasoline are known to co-produce $CO_2$ as a by-product when produced from carbon monoxide rich synthesis gas.

An advantage of the invention is that the amount of $CO_2$ being present in the synthesis gas feed stream and the amount of $CO_2$ being produced in the synthesis step is utilised efficiently in the production of power.

As mentioned above the gasoline synthesis is an exothermic reaction and removal of heat in gasoline production complicates and increases the number of equipment and increases the investment in a gasoline plant.

Power generation is convenient method of transforming the calories contained in the carbon monoxide rich synthesis gas. Gas turbines are efficiently converting the LHV of synthesis gas to electrical power. An important parameter in the gas turbine apparatus is the combustion chamber temperature and the adiabatic flue gas temperature during combustion. The flue gas temperature is partly determined by the degree of diluents, excess air or oxidant (e.g. enriched air or oxygen) used for the combustion of the fuel and partly by the fuel characteristics such as the inert level and the heating value of the fuel.

The process according to the invention does advantageously not require carbon dioxide removal. An additional advantage relates to the improved overall energy efficiency obtained due to the carbon dioxide by-product produced in significant amounts in the oxygenate synthesis contributing to an incremental power production in the gas turbine through its expansion (P-V work). Also, the additional amount of carbon dioxide produced in the gasoline synthesis serves as useful diluent for lowering the heat content in the fuel gas for the gas turbine thus reducing the requirement for additional diluent e.g. nitrogen from the air separation unit.

A broad embodiment of the invention relates to the combination of power production as commonly practiced in integrated gasification combined cycle (IGCC) plants with a co-production of gasoline.

DETAILED DESCRIPTION OF THE PREFERRED EMBODIMENTS

Figure 1:
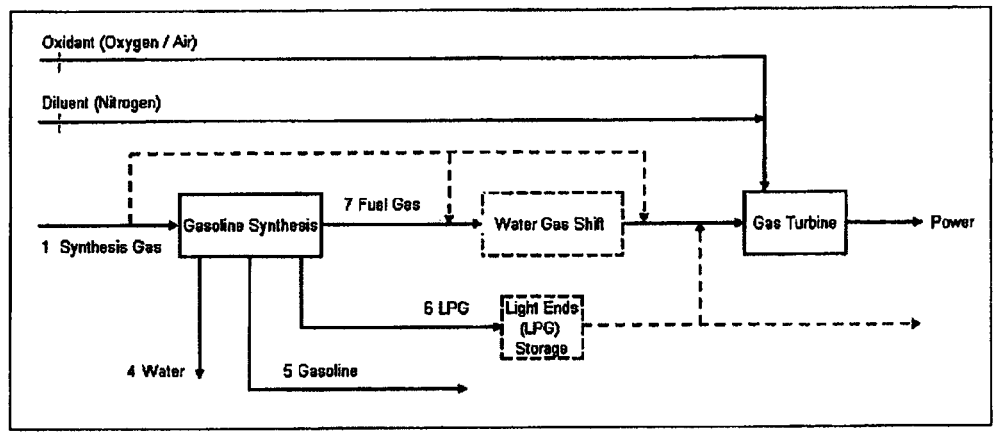
FIG. 1 illustrates a schematic of a gasoline synthesis process integrated into an IGCC plant, and according to an exemplary embodiment of the present invention.

FIG. 1 shows an overall configuration of a gasoline synthesis process integrated into an IGCC plant according to a specific embodiment of the invention.

The integration of a gasoline synthesis plant into the IGCC plant is realised in several ways. By reference to FIG. 1 the co-production of gasoline may take place either by feeding synthesis gas 1 in its entirety to the gasoline synthesis or only a fraction of the synthesis gas may be directed to the gasoline synthesis and the remainder passed directly or indirectly to the gas turbine together with tail gas 7 for combustion. In the latter process layout this stream and the stream of unconverted synthesis gas together with non-condensible hydrocarbons, inerts and carbon dioxide from the gasoline synthesis may conveniently be recombined prior to combustion in the gas turbine for the generation of power.

The process produces a fraction of non-condensible hydrocarbons being present in the stream of tail gas 7, a fraction of heavier hydrocarbons $C_5$ to $C_{11}$ being useful as gasoline 5 and a hydrocarbon fraction 6 of mainly $C_3$ to $C_4$ hydrocarbons that are conveniently recovered by conventional means of cooling and condensation. This fraction of light petroleum gas, LPG, represents a significant value as it may be traded at a relatively high price traditionally some 75 to 85% the price of gasoline. Alternatively, the LPG fraction may be stored in buffer tanks and conveniently serve as additional fuel for the gas turbines when electricity demand is high, under which conditions it may be more economic to use the LPG fraction for peak power production.

Another aspect of the invention relates to the degree of synthesis gas utilisation in the gasoline synthesis. The synthesis may be converted more or less efficiently depending on the number, configuration and type of reactors applied for the gasoline synthesis. This, in particular, concerns the oxygenate synthesis section of the process, as it is only in this section of the process that synthesis gas is converted, whereas in the gasoline synthesis section synthesis gas acts as a mere diluent for the conversion of oxygenates into gasoline. This will be illustrated by the following examples with reference to FIGS. 2 to 4 in the drawings.

FIGURES

Example 1

Figure 2:
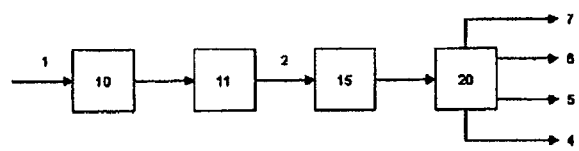
FIG. 2 illustrates a schematic view of the gasoline synthesis part of an integrated process, and according to an exemplary embodiment of the present invention.

FIG. 2 shows a specific embodiment of the invention. Heat exchangers and compressors are not shown. FIG. 2 shows the gasoline synthesis part of an integrated gasoline synthesis and IGCC plant. The gasoline synthesis step comprises two adiabatic oxygenate synthesis reactors 10,11 with inter-stage cooling (not shown) followed by an adiabatic oxygenate conversion reactor 15. Data on the essential process streams are shown in Table 1. The various hydrocarbon products are separated in unit 20.

Applying this process layout 11.9 T/h of gasoline in stream 5, a negligible amount of light ends, LPG in stream 6 and a fuel gas for combustion in stream 7 of 636,000 $Nm^3$/h are produced.

Stream 4 contains water being produced during the gasoline synthesis.

TABLE 1

| Composition | Position | | | | | | |
|---|---|---|---|---|---|---|---|
| (mole %) | 1 | 2 | 3 | 4 | 5 | 6 | 7 |
| $H_2$ | 37.7 | 35.8 | 35.4 | | | | 37.1 |
| CO | 45.6 | 35.6 | 35.5 | | | | 37.3 |
| $CO_2$ | 16.0 | 23.5 | 23.2 | | | | 24.3 |
| $CH_4$ | 0.6 | 0.6 | 0.6 | | | | 0.7 |
| $H_2O$ | 0.1 | 1.3 | 4.2 | 100 | | | |
| MeOH | | 0.8 | | | | | |
| DME | | 2.2 | | | | | |
| $C_2$-$C_4$ | | | 0.4 | | | 100 | 0.4 |
| $C_{5+}$ | | | 0.6 | | 100 | | 0.2 |
| Flow rate, | | | | | | | |
| $Nm^3$/h | 690895 | 659505 | 666773 | 27765 | 2680 | 118 | 636233 |
| Kg/h | | | | 22298 | 11949 | 277 | |

Example 2

Figure 3:
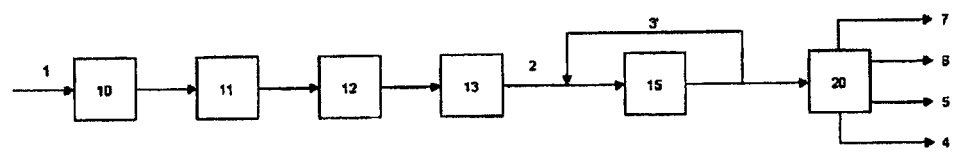
FIG. 3 illustrates a schematic view of the gasoline synthesis part of an integrated process, and according to another exemplary embodiment of the present invention.

FIG. 3 serves to illustrate another embodiment of the gasoline synthesis part of an integrated gasoline synthesis and IGCC plant. FIG. 3 shows a configuration comprising four adiabatic oxygenate synthesis steps 10,11,12,13 with interstage cooling (not shown) thus providing a higher conversion of synthesis gas into oxygenates than obtained in Example 1 followed by one oxygenate conversion (gasoline synthesis) step 15. This example includes a recycle of hot gasoline reactor effluent 3' back to the gasoline (oxygenate conversion) reactor in order to dilute the oxygenate stream 2. The various hydrocarbon products are separated in unit 20. There is obtained a stream of gasoline 5 of 25.4 T/h, 1.3 T/h of LPG 6 and an amount of fuel gas 7 of 566,386 $Nm^3$/h (Table 2). Water is withdrawn in stream 4.

TABLE 2

| Composition | Position | | | | | | |
|---|---|---|---|---|---|---|---|
| (mole %) | 1 | 2 | 3 | 4 | 5 | 6 | 7 |
| $H_2$ | 37.7 | 32.0 | 31.5 | | | | 34.1 |
| CO | 45.6 | 32.3 | 31.7 | | | | 34.3 |
| $CO_2$ | 16.0 | 28.11 | 27.5 | | | | 29.8 |
| $CH_4$ | 0.6 | 0.7 | 0.8 | | | | 0.9 |
| $H_2O$ | 0.1 | 1.1 | 6.6 | 100 | | | |
| MeOH | | 1.1 | | | | | |
| DME | | 4.7 | | | | | |
| $C_2$-$C_4$ | | | 0.7 | | | 100 | 0.6 |
| $C_{5+}$ | | | 1.2 | | 100 | | 0.2 |
| Flow rate, | | | | | | | |
| $Nm^3$/h | 690895 | 600483 | 613391 | 40677 | 5780 | 536 | 566386 |
| Kg/h | | | | 32666 | 25394 | 1282 | |

Example 2a

Optionally, the hot effluent being recycled to the oxygenate conversion step or part of it may pass a water gas shift conversion step (not shown in FIG. 3) with an additional water-gas shift catalyst in order to convert part of the water produced in the oxygenate conversion step into hydrogen and carbon dioxide. By this means the amount of non-condensible components in the product stream is increased resulting in less aqueous process condensate and a higher volumetric flow of high-pressure fuel gas to the gas turbine thus increasing the power production. The stream compositions resulting from the insertion of a water gas shift conversion step in the hot effluent recycle stream are shown in Table 2a.

TABLE 2a

| Composition | Position | | | | | | |
|---|---|---|---|---|---|---|---|
| (mole %) | 1 | 2 | 3 | 4 | 5 | 6 | 7 |
| $H_2$ | 37.7 | 32.0 | 32.6 | | | | 34.9 |
| CO | 45.6 | 32.3 | 30.6 | | | | 32.8 |
| $CO_2$ | 16.0 | 28.11 | 28.6 | | | | 30.6 |

TABLE 2a-continued

| Composition | Position | | | | | | |
|---|---|---|---|---|---|---|---|
| (mole %) | 1 | 2 | 3 | 4 | 5 | 6 | 7 |
| $CH_4$ | 0.6 | 0.7 | 0.8 | | | | 0.9 |
| $H_2O$ | 0.1 | 1.1 | 5.5 | 100 | | | |
| MeOH | | | 1.1 | | | | |
| DME | | | 4.7 | | | | |
| $C_2$-$C_4$ | | | 0.7 | | | 100 | 0.6 |
| $C_{5+}$ | | | 1.2 | | 100 | | 0.2 |
| Flow rate, | | | | | | | |
| $Nm^3/h$ | 690895 | 600483 | 613391 | 34018 | 5780 | 536 | 573086 |
| Kg/h | | | | 27319 | 25394 | 1282 | |

Example 3

Figure 4:
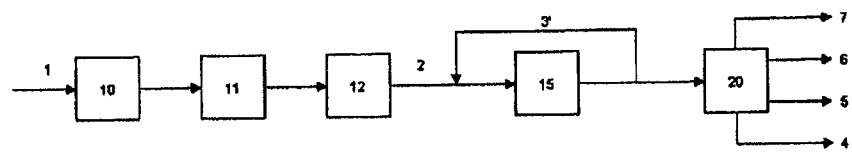
FIG. 4 illustrates a schematic view of the gasoline synthesis part of an integrated process, and according to yet another exemplary embodiment of the present invention.

FIG. 4 serves to illustrate yet another embodiment of the gasoline synthesis part of an integrated gasoline synthesis and IGCC plant. FIG. 4 shows a configuration comprising two adiabatic oxygenate synthesis steps 10,11 followed by one additional oxygenate synthesis step 12 where the heat of reaction from the oxygenate synthesis step is transferred to a heat absorption agent, e.g., by applying a boiling-water reactor. The efficient removal of the heat of reaction through the tubes walls of the cooled reactor leads to a significant increase in the amount of synthesis gas converted into oxygenates. The further conversion of oxygenates into hydrocarbons takes place in the oxygenate conversion 15 (gasoline synthesis). In this example the amount of hot effluent recycle 3' around the oxygenate conversion step to dilute the oxygenate feed is larger than that in the previous example, because the product stream from the cooled oxygenate synthesis reactor is significantly enriched in oxygenate. The various hydrocarbon products are separated in unit 20.

Thus, applying the process layout shown in FIG. 4, 69.5 T/h of gasoline and 11.7 T/h and light ends (LPG) and 320,256 Nm3/h of fuel gas are produced (Table 3).

TABLE 3

| Composition | Position | | | | | | |
|---|---|---|---|---|---|---|---|
| (mole %) | 1 | 2 | 3 | 4 | 5 | 6 | 7 |
| $H_2$ | 37.7 | 14.5 | 13.9 | | | | 17.9 |
| CO | 45.6 | 14.4 | 13.9 | | | | 17.9 |
| $CO_2$ | 16.0 | 50.7 | 47.4 | | | | 61.0 |
| $CH_4$ | 0.6 | 1.0 | 1.4 | | | | 1.9 |
| $H_2O$ | 0.1 | 0.8 | 17.7 | 100 | | | |
| MeOH | | | 1.4 | | | | |
| DME | | | 17.3 | | | | |
| $C_2$-$C_4$ | | | 2.0 | | | 100 | 1.7 |
| $C_{5+}$ | | | 3.7 | | 100 | | 0.2 |
| Flow rate, | | | | | | | |
| $Nm^3/h$ | 690895 | 421251 | 450944 | 79879 | 15962 | 4871 | 320256 |
| Kg/h | | | | 64148 | 69531 | 11676 | |

Example 3a

This example is similar to Example 3 except that the hot effluent recycle is passed through a water gas shift conversion step (not shown) with an additional water-gas shift catalyst before it is returned to the oxygenate conversion step. Like in example 2a the volumetric flow of high-pressure fuel gas to the gas turbine is increased. The stream compositions resulting from the insertion of a water gas shift conversion step in the hot effluent recycle stream are shown in Table 3a.

TABLE 3a

| Composition | Position | | | | | | |
|---|---|---|---|---|---|---|---|
| (mole %) | 1 | 2 | 3 | 4 | 5 | 6 | 7 |
| $H_2$ | 37.7 | 14.5 | 18.0 | | | | 22.0 |
| CO | 45.6 | 14.4 | 9.8 | | | | 12.0 |
| $CO_2$ | 16.0 | 50.7 | 51.4 | | | | 63.0 |
| $CH_4$ | 0.6 | 1.0 | 1.4 | | | | 1.7 |
| $H_2O$ | 0.1 | 0.8 | 13.7 | 100 | | | |
| MeOH | | | 1.4 | | | | |

TABLE 3a-continued

| Composition | Position | | | | | | |
|---|---|---|---|---|---|---|---|
| (mole %) | 1 | 2 | 3 | 4 | 5 | 6 | 7 |
| DME | | 17.3 | | | | | |
| $C_2$-$C_4$ | | | 2.0 | | | 100 | 1.1 |
| $C_{5+}$ | | | 3.7 | | 100 | | 0.2 |
| Flow rate, | | | | | | | |
| $Nm^3/h$ | 690895 | 421251 | 450944 | 61652 | 15962 | 4871 | 368511 |
| Kg/h | | | | 49511 | 69531 | 11676 | |

The examples presented above illustrate the flexibility in the gasoline synthesis with respect to integration into a power-producing IGCC plant and that by selecting different reactor configurations a wide range of conversions of synthesis gas into gasoline may be obtained.

The high per passage synthesis gas conversions that may be obtained relate to a significant extent to the favourable thermodynamics achieved by the combination of the methanol and dimethyl ether synthesis. The combination of the methanol and dimethyl ether syntheses should, however, not be considered as limiting with respect to the present invention. Thus, co-production of gasoline may also be achieved by combining a series of oxygenate synthesis steps comprising only the conversion of synthesis gas into methanol, albeit this embodiment does not provide as significant advantages as does the embodiment comprising the combined methanol and dimethyl ether syntheses. However, other combination of oxygenate synthesis steps may be applied favouring high single-passage conversions of synthesis gas, one example being the co-production of higher alcohols in the oxygenate synthesis step is another means of increasing the conversion per passage.

The invention claimed is:

1. A process for the preparation of hydrocarbon products and for the generation of power comprising the steps of:
   (a) providing a synthesis gas having a hydrogen to carbon monoxide ratio of between 0.1 and 1;
   (b) contacting the synthesis gas with one or more catalysts which together catalyse a reaction of hydrogen and carbon monoxide to oxygenates, the oxygenates comprising methanol and dimethyl ether with a ratio of the dimethyl ether to the methanol being higher than 2, the oxygenates further comprising carbon dioxide with a carbon dioxide content of above 20 mole %;
   (c) contacting the carbon dioxide containing oxygenate mixture at an inlet temperature of between 240 and 400° C. with a catalyst being active in the conversion of oxygenates to higher hydrocarbons and a fuel gas rich in carbon dioxide;
   (d) combusting the carbon dioxide rich fuel gas, optionally admixed with fresh carbon monoxide rich synthesis gas in a gas turbine combustion chamber to flue gas; and
   (e) expanding the flue gas stream through a gas turbine for the generation of power.

2. Process of claim 1, wherein the higher hydrocarbons comprise a fraction with $C_2$-$C_4$ hydrocarbons.

3. Process of claim 2, wherein at least part of the $C_2$-$C_4$ hydrocarbon fraction is admixed into the fuel gas upstream the gas turbine combustion chamber.

4. Process of claim 1, wherein the fuel gas is further contacted with an additional catalyst that is a water-gas shift catalyst upstream the gas turbine combustion chamber to convert part of water produced in step (c) into hydrogen and carbon dioxide.

5. Process of claim 1, wherein step (c) is carried out in at least two serial connected reactors with inter-cooling.

6. Process of claim 1, wherein step (c) is carried out under adiabatic manner.

7. Process of claim 1, wherein step (c) is carried out in one or more adiabatic reactors and in a subsequent boiling water reactor.

* * * * *

UNITED STATES PATENT AND TRADEMARK OFFICE
CERTIFICATE OF CORRECTION

PATENT NO. : 8,677,762 B2
APPLICATION NO. : 12/674272
DATED : March 25, 2014
INVENTOR(S) : Nielsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1072 days.

Signed and Sealed this
Twenty-ninth Day of September, 2015

Michelle K. Lee
*Director of the United States Patent and Trademark Office*